United States Patent [19]
Conrad et al.

[11] Patent Number: 5,773,308
[45] Date of Patent: Jun. 30, 1998

[54] PHOTOACTIVATABLE O-NITROBENZYL POLYETHYLENE GLYCOL-SILANE FOR THE PRODUCTION OF PATTERNED BIOMOLECULAR ARRAYS

[75] Inventors: David W. Conrad; Sara K. Golightley; John C. Bart, all of Alexandria, Va.

[73] Assignee: The United States of America as represented by the Secretary of the Navy, Washington, D.C.

[21] Appl. No.: 797,325

[22] Filed: Feb. 10, 1997

[51] Int. Cl.$^6$ .................... C07C 261/00; C07C 269/00; C08F 2/46; C08J 3/28
[52] U.S. Cl. ................ 436/527; 436/518; 435/6
[58] Field of Search .................... 436/527, 518; 435/6

[56] References Cited

U.S. PATENT DOCUMENTS

| | | | |
|---|---|---|---|
| 4,562,157 | 12/1985 | Lowe et al. | 435/291 |
| 5,143,854 | 9/1992 | Pirrung et al. | 436/518 |
| 5,252,743 | 10/1993 | Barrett et al. | 548/303.7 |
| 5,391,463 | 2/1995 | Ligler et al. | 430/272 |
| 5,405,783 | 4/1995 | Pirrung et al. | 436/518 |
| 5,412,087 | 5/1995 | McGall et al. | 536/24.3 |
| 5,424,186 | 6/1995 | Fodor et al. | 435/6 |
| 5,445,934 | 8/1995 | Fodor et al. | 435/6 |
| 5,451,683 | 9/1995 | Barrett et al. | 548/302.7 |
| 5,470,307 | 11/1995 | Lindall | 604/20 |
| 5,482,867 | 1/1996 | Barrett et al. | 436/518 |
| 5,489,678 | 2/1996 | Fodor et al. | 536/22.1 |
| 5,510,270 | 4/1996 | Fodor et al. | 436/518 |

FOREIGN PATENT DOCUMENTS

| | | |
|---|---|---|
| 4435758 | 7/1995 | Germany . |
| 9633971 | 10/1996 | WIPO . |

OTHER PUBLICATIONS

Bhatia et al, "New Approaches to Producing Patterned Biomolecular Assemblies" J. Am. Chem. Soc. 114, 4432–4433.

Matsuda et al, "Development of a Novel Protein Fixation Method with Micron–Order Precision" Langmuir 11, 2267–2271.

Bhatia et al "Fabrication of Surfaces Resistant to Protein Adsorption and Applicatin to two–Dimensional Protein Patterning" Analytical Biochemistry 208, 197–205.

Muller, W., et al, Science, vol. 262, Dec. 10, 1993, pp. 1706–1708.

Fodor, S.P.A. et al, Feb. 15, 1991, Science, vol. 251, pp. 767–773.

Holmes, C.R et al, Biopolymers, vol. 37, pp. 199–211, 1995.

Jennane, J. et al, Can. J. Chem., vol. 74, 1996, pp. 2509–2517.

Primary Examiner—James C. Housel
Assistant Examiner—Ginny Allen Portner
Attorney, Agent, or Firm—Thomas E. McDonnell; Ralph T. Webb

[57] ABSTRACT

O-nitrobenzyl analogs that include a photoremovable protecting group that resists the nonspecific adsorption of biomolecules and a linking group for attaching the o-nitrobenzyl analog to a substrate are disclosed. Also disclosed are methods for using o-nitrobenzyl analogs for creating patterned arrays of anti-ligands on a substrate so that a plurality of bioassays can be conducted simultaneously. In particular, the compounds disclosed are o-nitrobenzyl-polyethylene glycol-silanes, wherein the silane group serves to attach the compound to a substrate, the polyethylene glycol group resists the nonspecific adsorption of biomolecules. The o-nitrobenzyl group provides a photoactivatable functionality that allows the polyethylene glycol group to be selectively removed upon exposure to UV radiation and be replaced by an anti-ligand.

21 Claims, No Drawings

PHOTOACTIVATABLE O-NITROBENZYL POLYETHYLENE GLYCOL-SILANE FOR THE PRODUCTION OF PATTERNED BIOMOLECULAR ARRAYS

BACKGROUND OF THE INVENTION

1. Field of the Invention

The present invention relates to compounds and methods for attaching anti-ligands to a substrate. In particular, the invention relates to compounds and methods for creating patterned arrays of anti-ligands on a substrate so that a plurality of bioassays can be conducted simultaneously. The compounds are o-nitrobenzyl analogs that can be attached to a solid support and that include a photoremovable protecting group that resists the nonspecific adsorption of biomolecules. In particular, the compounds of the present invention are o-nitrobenzyl-polyethylene glycol-silanes, wherein the silane group serves to attach the compound to a substrate, the polyethylene glycol group resists the nonspecific adsorption of biomolecules and the o-nitrobenzyl group provides a photoactivatable functionality that allows the polyethylene glycol group to be selectively removed upon exposure to UV radiation and be replaced by an anti-ligand.

2. Description of the Related Art

Most current immunoassay techniques allow for the quantitation of only one individual sample analyte per experiment. Although sequential detection and identification strategies are possible, circumstances arise where the ability to detect and identify multiple analytes simultaneously within a single sample is highly advantageous. For example, the analysis of soil samples from sites contaminated with a variety of toxic chemicals could be performed faster, cheaper, and with less test-to-test variability if the analyses for multiple analytes could be performed concurrently rather than sequentially. Drug screening provides another area where one is usually interested in detecting and identifying more than one possible analyte. Finally, the clinical environment often requires the measurement of several related factors to accurately diagnose and treat many ailments. For example, several hormones need to be monitored to diagnose certain endocrine disorders. Similarly, a group of four or five factors are important for determination that a cardiac infarct has occurred. Simultaneous screening of factors is also desirable in other fields such as hematology, virology, and oncology.

The conventional approach to "multi-analyte" detection and identification has been to use multiple labels for key reagents in the immunoassay system to keep track of individual analytes. For example, dual assays have been developed in which one analyte was labeled with $^{125}$I and the other with $^{131}$I. The two isotopes were later measured independently. However, this technique is limited by the low number of useful radiolabels available. Multiple fluorophores or enzyme labels have also been used for a similar purpose. Quantitation using multiple fluorophores is also difficult due to differences in photobleaching rates, limitations on the number of fluorescent dyes with appropriate excitation and emission wavelengths, and fluorescence energy transfer. Using multiple enzymes as labels has the disadvantage of requiring multiple substrates and the correction for widely varying turnover rates. Even if these problems were overcome, the above methods would still be limited by the finite number of different non-interfering labels that could be employed in the same system on which multiple detection molecules are immobilized. It is would be impractical to try to develop a sensor of this type to detect and identify hundreds of different analytes simultaneously.

A better approach to multi-analyte detection and identification is to use spatial isolation of detectable elements on a solid support. In this approach, analytes are detected and identified not by which label is detected and identified, but rather by where on the substrate the label is positioned. Prior knowledge of the type of biomolecule or bioactive agent immobilized on the discrete region of the substrate surface allows for the identification and quantitation of multiple analytes.

Several broad strategies have been used in the development of patterned surfaces on which multiple antibodies are immobilized. The first strategy involves keeping the different antibodies physically separate throughout the immobilization procedure. The techniques employed range from simply applying the antibodies in individual stripes using a paintbrush to microwriting, microstamping or microspotting. These methods are simple and flexible, but do not allow for the production of high resolution (submicron) protein patterns. The second strategy uses microlithography to produce active substrate regions formed by selective removal or photochemical conversion of reactive monolayers to produce discrete regions for antibody immobilization.

U.S. Pat. No. 5,482,867 describes a method of immobilizing anti-ligands on a surface of a substrate by attaching to the substrate a caged biotin analog that has a photolabile protecting group. The protecting group is removeable by irradiation to convert the caged biotin analog into a biotin analog that is capable of non-covalently immobilizing an anti-ligand. Sequential steps of masking, irradiation and immobilization may be carried out to create a patterned substrate having different anti-ligands bound to different regions. Similar methods are described in U.S. Pat. No. 5,412,087, U.S. Pat. No. 5,391,463, U.S. Pat. No. 5,451,683, U.S. Pat. No. 5,489,678, U.S. Pat. No. 4,562,157, U.S. Pat. No. 5,316,784, U.S. Pat. No. 5,252,743 and U.S. Pat. No. 5,143,854.

One of the main problems encountered with most previously used methods for sequential protein immobilization in discrete locations has been the prevention of non-specific protein adsorption. This adsorption may occur at locations where a protein has been previously immobilized or at unactivated regions on a substrate surface. Extensive washing steps using salts and detergents have been required to partially alleviate these problems. The approaches described above begin with substrates that are, if unpassivated, quite susceptible to nonspecific protein adsorption.

SUMMARY OF THE INVENTION

Accordingly it is an object of this invention to provide a compound that can be used to modify a substrate so that the substrate becomes resistant to the adsorption of biomolecules and wherein the component of the compound that imparts resistance to the adsorption of biomolecules is photoremovable so that the compound becomes photoactivated for the covalent attachment of an anti-ligand. It is a further object of this invention to provide a method of using such a compound to create a patterned substrate having different anti-ligands bound to different regions.

These and other objects of the invention are accomplished by the structures and processes hereinafter described.

The compound of the present invention is an o-nitrobenzyl analog that has a photoremovable component that has a resistance to the adsorption of biomolecules and a linking group for attaching the compound to a substrate. When exposed to ultraviolet light, the photoremovable component is removed, creating an active site on the compound to which an anti-ligand can be covalently bonded. By using repeated sequential steps of masking, irradiating, binding an anti-ligand and washing, a patterned substrate can be created that can be used as a multianalyte array sensor for detecting different ligands simultaneously. The use of a photoactivatable o-nitrobenzyl analog and, in particular, o-nitrobenzyl polyethylene glycol (PEG)-silane in the creation of a patterned substrate has several distinct advantages over other chemical modifiers used for the (photo)immobilization of biomolecules. First, the unique composition of the o-nitrobenzyl PEG-silane combines both the ability to prevent non-specific biomolecule adsorption with the ability to become photoactivated by UV light so that micron-sized patterns can be created without interfering biomolecule adsorption. Second, the photochemical reaction which occurs during the patterning step also provides the reactive group which is used to bind the recognition molecule, thus eliminating the need for cross-linkers. In addition, the aldehyde moiety produced during photolysis is able to form stable, covalent bonds with a wide variety of biomolecules, including antibodies, enzymes, proteins, peptides, and DNA/RNA. Third, the density of recognition molecules which are incorporated in the sensor can be easily controlled through the extent of irradiation of the o-nitrobenzyl PEG-silane and/or via the concentration of the capture molecule (anti-ligand) applied during the sensor preparation. Fourth, the o-nitrobenzyl PEG-silane is quite resistant to chemical and biological degradation, making long-term storage of the sensor precursors facile, and eliminating the problems that other biosensors have with bacterial or microbial degradation. And finally, the o-nitrobenzyl PEG-silane is only photoactive in the UV region of the spectrum, so the sensor can be stored and used without taking special precautions to prevent exposure to normal room lighting.

DETAILED DESCRIPTION OF THE PREFERRED EMBODIMENTS

The present invention relates to a compound and method for attaching an anti-ligand to a substrate and more particularly, to a method of using the compound to create a patterned substrate having different anti-ligands bound to different regions. The anti-ligand used in the present invention is any complex or molecule that has, prior to attachment, a primary amine and includes, but is not limited to antibodies, enzymes, DNA or RNA, genetically engineered proteins/peptides, ligands for cell surface receptors, hormones, antibiotics, antigens, fluorescent molecules, phosphorescent molecules, luminescent molecules, chemiluminescent molecules, bioluminescent molecules, lanthanides, actinides, metal chelators, inorganic metal complexes, redox-active metal complexes or organic compounds, and inorganic or organic catalysts. Any prospective anti-ligand that does not contain a primary amine can be modified by any known method to add a primary amine to it. Preferably, the anti-ligand is an antibody or antibody fragment. The substrate is any solid surface including glass, silicon, fused silica, plastics, particularly polymers with surface hydroxyl groups, metals, metal oxides and ceramics. The substrate is not limited to planar surfaces but can also be beads, capillaries or ELISA plate wells. Examples of suitable anti-ligands and substrates for the practice of this invention may be found in U.S. Pat. No. 5,482,867, U.S. Pat. No. 5,412,087, U.S. Pat. No. 5,391,463, U.S. Pat. No. 5,451,683, U.S. Pat. No. 5,489,678, U.S. Pat. No. 4,562,157, U.S. Pat. No. 5,316,784, U.S. Pat. No. 5,252,743 and U.S. Pat. No. 5,143,854, the entire disclosures of which are herein incorporated by reference. The above references also describe methods of using patterned substrates for sensing applications including multianalyte immunological assays.

The compound of the present invention is a protected o-nitrobenzyl analog represented by the formula:

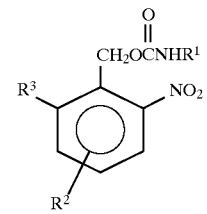

wherein $R^1$ is a component that has a resistance to nonspecific biomolecule adsorption, $R^2$ is a linear linking group having a distal end that is capable of forming a covalent bond with a substrate, and $R^3$ is $NO_2$ or H. By the provision that $R^1$ has a resistance to nonspecific biomolecule adsorption, it is meant that the component resists adsorption by any biomolecule or compound, particularly by any biomolecule or compound wherein adsorption would interfere with the construction or resolution of a patterned array. For example, the component should resist nonspecific adsorption by anti-ligands, particularly proteins, used in the construction of a patterned array and should resist nonspecific adsorption by analytes sought to be detected in sensing applications. The $R^1$ group should be large enough to affect the surface properties of the substrate to which the o-nitrobenzyl analog is attached and to cause the surface as a whole to have a resistance to the nonspecific adsorption of biomolecules. $R^1$ is preferably —$(CH_2CH_2O)_nCH_3$ (a polytheylene glycol group) where n is an integer from about 6 to about 300. R2 can be any linear linking group known in the art for forming covalent bonds with a substrate and is preferably —$O(CH_2)_mSiCl_3$, —$O(CH_2)_mSi(OCH_3)_3$ or —$O(CH_2)_mSi(OCH_2CH_3)_3$ where m is an integer from about 9 to about 25.

Compounds of the above formula may be synthesized, for example, by the reaction scheme shown in Example 1 for the synthesis of o-nitrobenzyl PEG-silane or by any other methods known in the art for joining substituents to an o-nitrobenzyl ring. An example of such a synthesis is shown in Example 1. In the practice of the invention, the compound is covalently attached to a substrate to form a layer thereon, creating a modified surface that has a resistance to the nonspecific adsorption of biomolecules. Irradiating the modified substrate with ultraviolet light removes the carbamate protecting group from the compound to form a unprotected o-nitrosobenzyl analog represented by the formula:

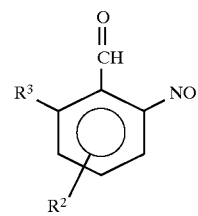

wherein $R^3$ is $NO_2$ or H and $R^2$ is a linear linking group having a distal end that is covalently bonded to the substrate. Irradiation with ultraviolet light can be done by any known means including by using an HgXe lamp as described in the examples below or by using an excimer laser (193 or 248 nm). Advantages associated with the use of an excimer laser include: 1) less light scattering and hence better resolution during irradiation, 2) the ability to work in projection mode, removing the need for a mask and minimizing problems of cross-contamination caused by reusing the mask, and 3) more flexibility in the types of patterns that can be formed by laser "writing" using a movable substrate stage.

The aldehyde group on the unprotected o-nitrosobenzyl analog may then react with a primary amine on the anti-ligand to form an imine (Schiff base). The imine may be reduced by, for example, sodium cyanoborohydride to form a secondary amine. The o-nitrosobenzyl analog then serves as a bridging group, covalently bound to both the substrate and the anti-ligand, as represented by the formula:

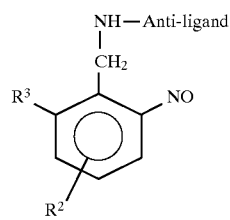

wherein $R^3$ is $NO_2$ or H and $R^2$ is a linear linking group having a distal end that is covalently bonded to the substrate.

By using a mask, the irradiation with ultraviolet light can be limited to a predefined region of the substrate and only those compounds that lie within the predefined region are converted to the unprotected o-nitrosobenzyl analog and bind the anti-ligand. The modified substrate may then be washed to remove unbound anti-ligand. Because the o-nitrobenzyl analog includes a component that has a resistance to nonspecific biomolecule adsorption, the adsoption of the anti-ligand on non-irradiated regions of the modified substrate is minimized. Using photopatterning, well-defined micrometer-sized patterns can be produced. The process steps of masking, irradiating, binding and washing can be repeated on different predefined regions with different anti-ligands to create a patterned substrate that can be used as a multianalyte array sensor for detecting different ligands simultaneously. Detection of the binding of different ligands to the different anti-ligands on a multianalyte array sensor may be accomplished by any means known in the art including the use of fluorescent dyes (for example, Cy5), chemiluminescent dyes, electrochemiluminescent dyes, radioactive labels, or any other common markers. The choice of the label may be selected on the basis of the specific conditions in which the array sensor is to be operated in order to maximize sensitivity for the analytes to be measured. Another alternative concerns the types of biomolecules used to form the sensor array. For example, instead of using only antibodies targeted to different antigens, groups of antibodies exhibiting differential affinities to the same antigen could also be used. The obvious advantage of operating the sensor in this configuration would be the availability of several independent signals to help confirm the presence of analytes of interest. False positives arising from cross-reactivity problems might also be distinguishable, since it is unlikely that structurally-related compounds would show identical binding constants with the group of antibodies. Pattern recognition software could be used to discriminate reactions of arrays of binding molecules which are semi-selective. Image analysis programs could look for a specific pattern of fluorescence emanating from individual antibody groups before signaling the presence of the analyte.

Preferably, the o-nitrobenzyl analog used to modify the substrate is represented by the formula:

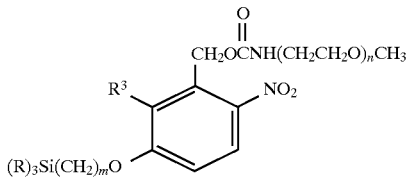

wherein R is a leaving group, m is an integer from about 9 to about 25, n is an integer from about 6 to about 300 and $R^3$ is $NO_2$ or H. Preferably R in the above formula is Cl, $OCH_3$ or $OCH_2CH_3$. The above compound, since it contains a silane group and a polyethylene glycol (PEG) group, may also be referred to as an o-nitrobenzyl polyethylene glygol silane or an o-nitrobenzyl PEG-silane. The silane group readily attaches to substrates to form a compound of the formula:

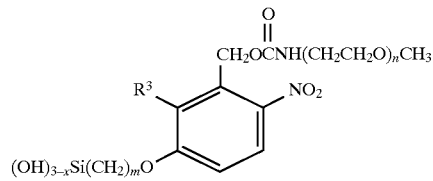

where $R_3$, n and m are as defined above and where Si is covalently bonded to the substrate by at least one bond. In the above formula, x represents the number of bonds between Si and the substrate. Due to the presence of the polyethylene glycol group, a substrate modified by the attachment of the above compound has a resistance to the adsorption of biomolecules. When the compound is irradiated with ultraviolet light, the polyethylene group is released from the compound and an unprotected o-nitrosobenzyl analog is formed which can be used to bind an anti-ligand as described above.

Having described the invention, the following examples are given to illustrate specific applications of the invention, including the best mode now known to perform the invention. These specfic examples are not intended to limit the scope of the invention described in this application.

EXAMPLE 1:

Synthesis of o-nitrobenzyl PEG-Silane and Creation of a Modified Substrate

Synthesis of a o-nitrobenzyl PEG-silane of the above formula wherein $R^3$ is H and m=11 was achieved in three steps. First, 5-hydroxy-2-nitrobenzyl alcohol I in 0.3 NaOH was refluxed for four days with undecylenic bromide II (dissolved in $CH_2Cl_2$) in the presence of benzyltributylammonium bromide to form 2-nitro-5-(10-undecenyloxy) phenylmethanol III according to the following reaction scheme:

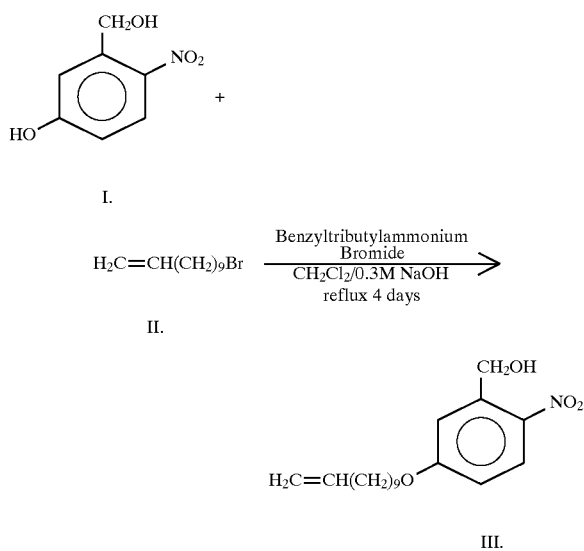

Second, the polyethylene glycol (PEG) chain was attached to the photoactive o-nitrobenzyl alcohol III via the reaction of a commercially available PEG-isocyanate with the deprotonated alcohol according to the following reaction scheme:

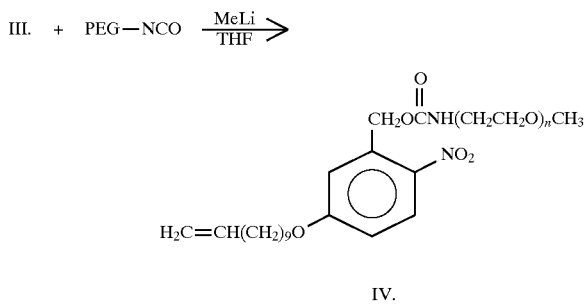

Finally, the carbamate IV was exposed for 1 hour at room temperature to a solution of trichlorosilane in toluene (1:1, v/v) the presence of platinum divinyltetramethyldisiloxane (catalyst) to yield the final product V as in the following reaction scheme:

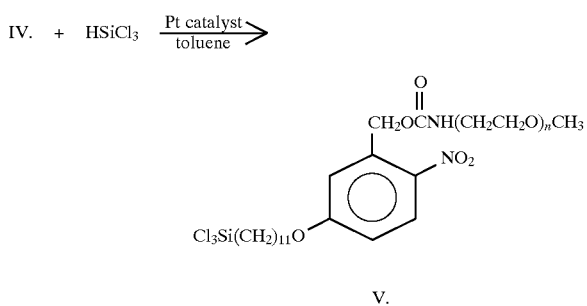

Deposition of the o-nitrobenzyl PEG-silane onto the desired support medium (glass, fused silica, silicon wafer, etc.) was achieved by dissolution of the o-nitrobenzyl PEG-silane in toluene followed by submersion of the support medium in the o-nitrobenzyl PEG-silane solution (0.03 mg/mL) for 2 hours at 55° C. The substrate was then rinsed twice in anhydrous toluene and dried in an oven at 110° C. for 5 minutes.

EXAMPLE 2:

Irradiation of the Modified Substrate to Produce Surface Aldehydes o-Nitrobenzyl PEG-silane was attached to a fused silica slide by the procedure described above. The UV-vis spectrum of the silane (mono)layer was measured from 190 to 400 nm. The modified substrate was then exposed to deep-UV (broadband, power at 220 nm=10.5 mW cm$^{-2}$) for 3 min. After irradiation for 30 seconds, 60 seconds and 180 seconds, the spectrum was measured again and compared to the unirradiated spectrum. Analysis showed the peak at 311 nm (due to the nitro group) decreased after irradiation. This spectral change corresponds to the expected conversion of the nitro group to a nitroso group with the concomitant production of surface aldehydes. The presence of photogenerated aldehyde functionalities was also confirmed by a positive 2,4-DNPH test.

EXAMPLE 3:

Immobilization of Fluorescein-Labeled IgG

A o-nitrobenzyl PEG-silane-modified substrate created by the process described in Example 1, above, was irradiated through a copper hexagonal TEM mask using a 150 W HgXe source (hv=220 nm, 10.5 mW/cm$^2$) for 3 minutes. The substrate was rinsed with water and immersed in a solution of antibody (fluorescein-labeled goat IgG, 1 mg/mL in 50 mM sodium acetate buffer, pH=4.5) for 2 hours. Then 1 mg of sodium cyanoborohydride (NaBH$_3$CN) was added and allowed to react an additional 10 minutes. The substrate was rinsed in water for 30 seconds. After drying in a jet of N$_2$, the substrate was visualized by laser-scanning confocal fluorescence microscopy using excitation at 488 nm and emission >510 nm. The fluorescent micrograph showed dark areas that correspond to regions blocked from deep-UV light by the mask. Since photoactivation did not occur in these regions, there was little or no binding of fluorescently-labeled antibodies at these sites. The fluorescent micrograph showed light areas that correspond to irradiated regions (open hexagons) and showed increased fluorescence in these areas due to the attachment of fluorescein-labeled antibodies. The average contrast ratio between irradiated and unirradiated regions in this micrograph was 10:1.

EXAMPLE 4:

Sequential Immobilization of Anti-Rat and Anti-Rabbit-IgGs on o-nitrobenzyl PEG-Silane Modified Surface.

Substrate preparation and o-nitrobenzyl PEG-silane deposition were as in Example 1. Three identical silane-modified slides were irradiated using dark field slit (50 μm) masks for 3 minutes. After rinsing with water for 30 seconds, they were exposed to a solution of anti-rat IgG (0.25 mg/mL in sodium acetate buffer, pH 4.5) and sodium cyanoborohydride (1 mg/mL in sodium acetate buffer, pH 4.5) for 1 hour. They were then rinsed in water for 30 seconds. The masks were again placed over the slides, but this time the slits were rotated 90° relative to the previously irradiated region. The slides were irradiated for a second time. After rinsing in water for 30 seconds, they were exposed to a solution anti-rabbit IgG (0.25 mg/mL in sodium acetate buffer, pH 4.5) for 1 hour. The substrates were rinsed as described earlier. One slide was exposed to a solution of fluorescein-labeled rat IgG (1 mg/ml, in sodium acetate buffer, pH 4.5), a second slide was exposed to a solution of fluorescein-labeled rabbit IgG (1 mg/mL in sodium acetate buffer, pH 4.5), and the third was sequentially exposed to fluorescein-labeled rat IgG and fluorescein-labeled rabbit IgG (each 1 mg/mL in sodium acetate buffer, pH 4.5). After 15 minutes, the slides were rinsed with water for 30 seconds and dried in a jet of Ar. When the slides were imaged using the laser-scanning confocal fluorescence microscope, the slide exposed to fluorescein-labeled rat IgG showed only one bright stripe when scanned at 488 nm (appropriate excitation line for fluorescein). The stripe was located in the region in which anti-rat IgG was immobilized. The slide exposed to fluorescein-labeled rabbit IgG also showed only one bright stripe when scanned at 488 nm. The slide exposed to both fluorescein-labeled rat IgG and fluorescein-labeled rabbit IgG showed two bright stripes as would be expected. This experiment demonstrates not only the possibility of sequential attachment, but it also illustrates that the immobilized antibodies are able to bind their respective antigens. Fluorescence from non-specific binding of fluorescently-labeled antibodies to unirradiated regions of the silane-modified surface was very low and was estimated to be less than 10% (based on pixel intensity) of that exhibited by antibodies bound in irradiated regions.

EXAMPLE 5:

In Situ Irradiation and Antibody Immobilization Experiment.

o-nitrobenzyl PEG-silane was deposited on a fused silica slide as described in Example 1. The substrate was placed in a freezer at $-10°$ C. for 5 minutes and then allowed to warm to room temperature. As this occurred, condensation formed on the surface of the substrate so that the concentrated antibody solution was never applied to a dry silane surface. 20 μL of NaBH$_3$CN (2 mg/mL in 50 mM sodium acetate buffer, pH 4.5) and 20 μL of donkey anti-goat IgG (0.5 mg/mL in 10 mM phosphate-buffered saline, pH7.4, PBS, containing 0.3% Tween 20) were added to the moist substrate and then the mask was placed on top of the solutions. The substrate was then irradiated by a 75 W HgXe lamp (filtered through a 320 nm longpass filter) for 20 minutes. The antibody/reductant solution was allowed to remain in contact with the substrate for an additional 120 minutes after irradiation was complete. After the mask was removed, the substrate was rinsed with PBS containing 0.3% Tween 20 and then submersed in a solution of the same for 30 minutes. The substrate was removed from the PBS/Tween wash, but not allowed to dry completely. 40 μL of a sulfoindocyanine (Cy5) dye-labeled goat IgG (0.1 mg/mL in PBS containing 0.05% Tween 20) was added to the substrate and then covered with another silane-coated fused silica slide and allowed to react for 60 minutes. After removal of the cover slide, the excess antibody was washed off with PBS containing 0.3% Tween 20, followed by a rinse with water. Finally, the slide was dried under a jet of Ar and the fluorescent pattern was imaged using a CCD detector with a 635 nm laser excitation source. The pattern from the mask was visualized on the slide, demonstrating that immobilization and irradiation steps of the procedure can be performed concurrently.

EXAMPLE 6:

Multiple Analyte Detection Using an Antibody Array.

O-nitrobenzyl PEG-silane was deposited on a fused silica slide as in Example 1. The slide was then covered with a dark field mask which has a single 2 mm square window offset from the center which allows four squares to be irradiated on the substrate by simply rotating the mask by $90°$ a total of three times. After irradiating the slide for 10 minutes using a 75 W HgXe lamp, the slide was rinsed with water, dried under a jet of argon, and then cooled in a freezer to $-10°$ C. A 20 μL drop of 2 mg/mL sodium cyanoborohydride in 50 mM sodium acetate buffer (pH=4.5) was added to the cooled slide, followed by a 20 μL drop of 0.5 mg/mL donkey α-sheep IgG in PBS. This mixture was then covered with a Bovine Serum Albumin (BSA)-coated glass slide, such that the entire o-nitrobenzyl PEG-silane surface was covered by a thin layer of the antibody/reductant solution and allowed to react for 30 minutes. The slide was then rinsed in PBS and then the mask was added such that a thin layer of PBS was trapped between the mask and silane-coated slide. A second irradiation was then performed as previously described above. After rinsing the slide was PBS, the still wet slide was treated with the reductant and antibody solutions as described above, except for the substitution of donkey α-chicken IgG for donkey α-sheep IgG. These steps were then repeated twice more, using donkey α-rat and finally donkey α-rabbit as the capture antibodies. After the final 30 minutes reaction between the capture antibody and the irradiated slide, the substrate was washed with PBS containing 0.3% Tween 20, followed by a 10 minute soak in the same solution. Application of the Cy5-labeled antigens was performed sequentially using the procedure outlined below. A 40 μL drop of 0.1 mg/mL of Cy5-labeled IgG (sheep, chicken, rat, or rabbit) in PBS containing 0.03% Tween 20 was applied to the wet slide and then covered with a BSA-coated slide and allowed to react for 30 minutes. After rinsing the slide in PBS containing 0.3% Tween 20, the slide is either exposed to another labeled antigen, or washed with water and then dried under a jet of argon. Imaging was performed as described in Example 5. The multianalyte image showed square areas which appear white where irradiation occurred, and thus indicate that Cy5-labeled IgGs were bound by all four respective capture antibodies.

EXAMPLE 7:

Immobilization of Antibodies Inside Capillaries.

Capillaries (made of either glass or fused silica) were sonicated in HPLC grade methanol for 3 minutes, dried with argon, and then plasma cleaned for 5 minutes at approx. 100 mtorr. The o-nitrobenzyl PEG-silane was then deposited onto the inner surface of the capillaries (via capillary action after dipping the tip of the capillary into a solution of the silane) following the procedure outlined in Example 1, with the exception that the silane was allowed to react with the capillaries for 3.5 to 4.5 hours instead of 2 hours. The silane solution was then ejected from the tip of the capillary via a jet of argon gas. The capillary was then filled with toluene to rinse out the silane solution and then dried with argon. This rinse procedure was performed a total of 10 times, and then the capillaries were cured in an oven at $120°$ C. for 5 minutes. A capillary having a width of 2 mm was covered with a variable width line mask having the narrowest bars being 500 μm wide and then irradiated 10 minutes with a 75 W HgXe lamp. After rinsing the capillary with water and drying with argon, the capillary was placed in a test tube containing 20 μL of 2 mg/mL NaBH$_3$CN in 50 mM sodium acetate buffer (pH=4.5) and 20 μL of 0.5 mg/mL Cy5-labeled rat IgG in PBS. The reductant/antibody solution was allowed to remain in contact with the irradiated capillary for 30 minutes before being rinsed with PBS containing 0.3% Tween 20 (twice), followed by five rinses of the capillary with water. The capillary was then dried using argon and imaged using a CCD detector. The CCD image shows areas of variable width corresponding to areas that were irradiated through the variable width mask. The areas appear white and thus indicate that Cy5-labeled antibody is present.

Obviously, many modifications and variations of the present invention are possible in light of the above teachings. It is therefore to be understood that, within the scope of the appended claims, the invention may be practiced otherwise than as specifically described.

What is claimed is:

1. A compound having the formula:

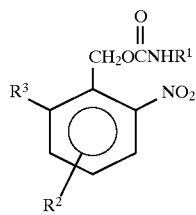

wherein $R^1$ is —$(CH_2CH_2O)_nCH_3$, where n is an integer from about 6 to about 300, $R^2$ is a linear linking group having a distal end that is capable of forming a covalent bond with a substrate, and $R^3$ is $NO_2$ or H.

2. The compound of claim 1 wherein $R^2$ is —$O(CH_2)_mSiCl_3$, —$O(CH_2)_mSi(OCH_3)_3$ or —$O(CH_2)_mSi(OCH_2CH_3)_3$ where m is an integer from about 9 to about 25.

3. A compound having the formula:

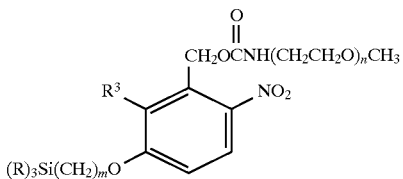

wherein R is a leaving group, m is an integer from about 9 to about 25, n is an integer from about 6 to about 300 and $R^3$ is $NO_2$ or H.

4. The compound of claim 3 wherein R is Cl, $OCH_3$, or $OCH_2CH_3$.

5. A modified substrate having a compound covalently bonded thereto, the compound having the formula:

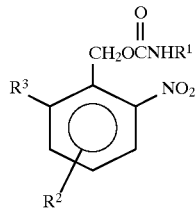

wherein $R^1$ is —$(CH_2CHO)_nCH_3$, where n is an integer from about 6 to about 300, $R^2$ is a linear linking group having a distal end that is covalently bonded to the solid substrate and $R^3$ is $NO_2$ or H.

6. The modified substrate of claim 5 wherein $R^2$ is —$O(CH_2)_mSi(OH)_{3-x}$ where Si forms at least one covalent bond with the substrate and x is an integer between 1 and 3 representing the number of covalent bonds between Si and the substrate.

7. A patterned substrate for performing a plurality of biological assays simultaneously utilizing the compound of claim 2, wherein, the patterned substrate comprising a plurality of predefined regions, each predefined region having bound thereto a compound of the formula:

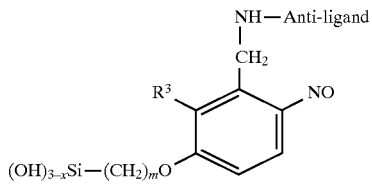

wherein Si forms at least one covalent bond with the predefined region of the substrate and x is an integer between 1 and 3 representing the number of covalent bonds between Si and the predefined region of the substrate, m is an integer from about 9 to about 25, $R^3$ is $NO_2$ or H and wherein the anti-ligand is different in each predefined region of the substrate.

8. The patterned substrate of claim 7 wherein the patterned substrate is glass, fused silica, silicon, ceramic, metal oxide or a polymer having surface hydroxyl groups.

9. The patterned substrate of claim 7 wherein the patterned surface is an ELISA plate well.

10. The patterned substrate of claim 7 wherein the patterned substrate is the interior of a capillary tube.

11. The patterned substrate of claim 7 wherein each anti-ligand is an antibody.

12. A method for attaching a plurality of anti-ligands having different binding specificities to predefined regions on a substrate, the method comprising the steps of (a) covalently binding to the substrate a protected o-nitrobenzyl analog wherein the anolog is the compound of claim 1, having a photoremovable protecting group that has a resistance to nonspecific biomolecule adsorption, to create a modified substrate having a resistance to nonspecific biomolecule adsorption (b) irradiating the protected o-nitrobenzyl analog on a first predefined region of the substrate to remove the photoremovable protecting group and to form unprotected o-nitrosobenzyl analog having a reactive group capable of covalently binding an anti-ligand, (c) reacting the unprotected o-nitrosobenzyl analog with an anti-ligand to covalently bind the anti-ligand to the unprotected o-nitrosobenzyl analog to form a bridging o-nitrosobenzyl analog that is covalently bound to the first predefined region of the substrate and that is covalently bound to the anti-ligand, (d) washing the substrate to remove unbound anti-ligand, whereby steps (a) to (d) result in a first predefined region of the modified substrate having a bridging o-nitrosobenzyl analog covalently bound thereto and having an anti-ligand bound to the bridging o-nitrosobenzyl analog, and a remainder region of the modified that has not been irridiated and has the protected o-nitrobenzyl analog bound thereto, the remainder region having a resistance to nonspecific biomolecule adsorption, (e) repeating steps (b) to (d) at least one additional time on a different region of the substrate with a different anti-ligand.

13. The method of claim 12 wherein the unprotected o-nitrosobenzyl analog is a compound of the formula:

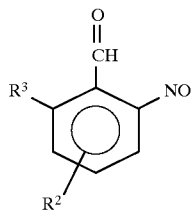

wherein $R^3$ is $NO_2$ or H and $R^2$ is a linear linking group having a distal end that is covalently bonded to the first predefined region of the substrate, and wherein the bridging o-nitrosobenzyl analog is a compound of the formula:

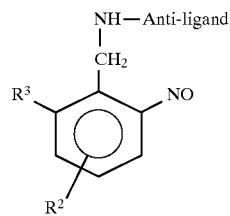

wherein $R^3$ is $NO_2$ or H and $R^2$ is a linear linking group having a distal end that is covalently bonded to the first predefined region of the substrate.

14. A method for attaching a plurality of anti-ligands having different binding specificities to predefined regions on a substrate, the method comprising the steps of (a) covalently binding to the substrate a protected o-nitrobenzyl analog of the formula:

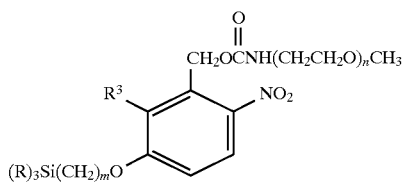

wherein R is a leaving group, m is an integer from about 9 to about 25, and n is an integer from about 6 to about 300, and $R^3$ is $NO_2$ or H to form a modified substrate having bound thereto a compound of the formula:

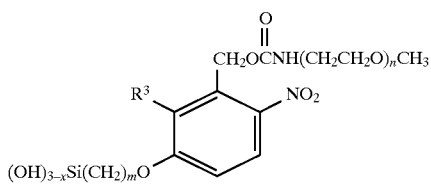

wherein Si forms at least one covalent bond with the substrate and x is an integer between 1 and 3 representing the number of covalent bonds between Si and the substrate, m is an integer from about 9 to about 25, and n is an integer from about 6 to about 300, and $R^3$ is $NO_2$ or H, (b) irradiating the protected o-nitrosobenzyl analog on a first prefined region of the modified substrate to form unprotected o-nitrosobenzyl analog of the formula:

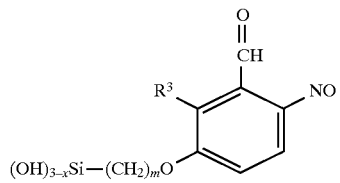

wherein Si forms at least one covalent bond with the first predefined region of the modified substrate and x is an integer between 1 and 3 representing the number of covalent bonds between Si and the first predefined region of the modified substrate and m is an integer from about 9 to about 25 and $R^3$ is $NO_2$ or H, (c) reacting the unprotected o-nitrosobenzyl analog with an anti-ligand to covalently bind the anti-ligand to the unprotected o-nitrosobenzyl analog to form a bridging o-nitrosobenzyl analog of the formula:

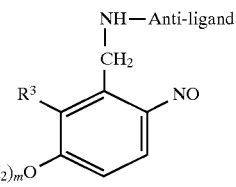

where Si forms at least one covalent bond with the first predefined region of the modified substrate and x is an integer between 1 and 3 representing the number of covalent bonds between Si and the first predefined region of the modified substrate, m is an integer from about 9 to about 25 and $R^3$ is $NO_2$ or H (d) washing the substrate to remove unbound anti-ligand, (e) repeating steps (b) to (d) at least one additional time on a different region of the modified substrate with a different anti-ligand.

15. The method of claim 14 wherein the substrate is glass, fused silica, silicon, ceramic, metal oxide or a polymer having surface hydroxyl groups.

16. The method of claim 14 wherein the substrate is an ELISA plate.

17. The method of claim 14 wherein the substrate is the interior of a capillary tube.

18. The method of claim 14 wherein each anti-ligand is an antibody.

19. The method of claim 14 wherein R is Cl, $OCH_3$ or $OCH_2CH_3$.

20. A patterned substrate for performing a plurality of biological assays simultaneously, made by a process comprising the steps of:

(a) covalently binding to the substrate a protected o-nitrobenzyl analog of the formula:

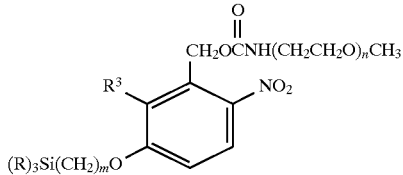

wherein R is a leaving group, m is an integer from about 9 to about 25, and n is an integer from about 6 to about 300, and $R^3$ is $NO_2$ or H, to form a modified substrate having bound thereto a compound of the formula:

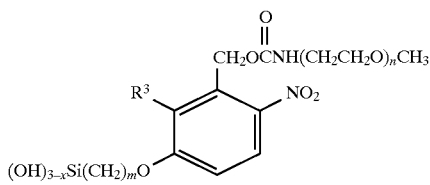

wherein Si forms at least one covalent bond with the substrate and x is an integer between 1 and 3 representing the number of covalent bonds between Si and the substrate, m is an integer from about 9 to about 25, and n is an integer from about 6 to about 300, and $R^3$ is $NO_2$ or H, (b) irradiating the protected o-nitrobenzyl analog on a first predefined region of the substrate to form unprotected o-nitrosobenzyl analog of the formula:

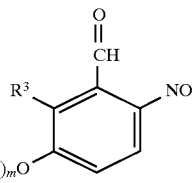

where Si forms at least one covalent bond with the first predefined region of the modified substrate and x is an integer between 1 and 3 representing the number of covalent bonds between Si and the first predefined region of the modified substrate and m is an integer from about 9 to about 25 and $R^3$ is $NO_2$ or H, (c) reacting the unprotected o-nitrosobenzyl analog with an anti-ligand to covalently bind the anti-ligand to the unprotected o-nitrosobenzyl analog to form a bridging o-nitrosobenzyl analog of the formula:

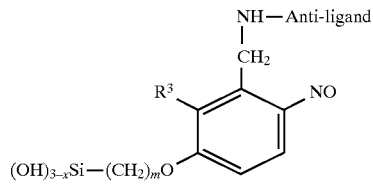

where Si forms at least one covalent bond with the first predefined region of the modified substrate and x is an integer between 1 and 3 representing the number of covalent bonds between Si and the first predefined region of the modified substrate and m is an integer from about 9 to about 25 and $R^3$ is $NO_2$ or H, (d) washing the substrate to remove unbound anti-ligand, (e) repeating steps (b) to (d) at least one additional time on a different region of the modified substrate with a different anti-ligand.

21. The patterned substrate of claim 20 wherein R is Cl, $OCH_3$ or $OCH_2CH_3$.

* * * * *